United States Patent [19]
Jester

[11] Patent Number: 5,575,631
[45] Date of Patent: Nov. 19, 1996

[54] CURVILINEAR PERISTALTIC PUMP

[75] Inventor: Rogelio Blanco Jester, Mexicali, Mexico

[73] Assignee: Ahmad-Maher Moubayed, Mission Viejo, Calif.

[21] Appl. No.: 615,704

[22] Filed: Mar. 12, 1996

[51] Int. Cl.⁶ .................................................. F04B 43/08
[52] U.S. Cl. ......................................................... 417/474
[58] Field of Search ................................... 417/474, 478, 417/479, 480; 604/153

[56] References Cited

U.S. PATENT DOCUMENTS

| | | | |
|---|---|---|---|
| 3,127,845 | 4/1964 | Voelcker | 417/478 |
| 5,217,355 | 6/1993 | Hyman et al. | 417/474 |

FOREIGN PATENT DOCUMENTS

| | | | |
|---|---|---|---|
| 2152352 | 4/1973 | Germany . | |
| 582797 | 9/1958 | Italy . | |
| 853157 | 8/1981 | U.S.S.R. | 417/474 |
| 941672 | 7/1982 | U.S.S.R. | 417/474 |

*Primary Examiner*—Timothy Thorpe
*Assistant Examiner*—Peter G. Korytnyk
*Attorney, Agent, or Firm*—John R. Duncan; Frank D. Gilliam

[57] ABSTRACT

A curvilinear peristaltic pump for pumping liquids through a resilient tube. The pump includes a curved concave platen against which a resilient tube is placed. A multi lobed cam is positioned adjacent to the platen and tube. A plurality of pump fingers are mounted between the tube and cam in a manner permitting radial movement of the pump fingers. As the cam rotates, the fingers are pressed toward the tube sequentially so as to pump liquid through the tube. The lobe end presses the tube sufficiently to occlude the tube and prevent back flow without over pressing and damaging the tube. A transverse pinch finger is provided on each pump finger, extending from the tube pressing face of each pump finger. At the tube occluding position, the pump finger nearly occludes the tube and the pinch finger completes occlusion without pressing the tube beyond the fully occluded position. A fixed or slidable spring pressed pinch finger may be used.

20 Claims, 2 Drawing Sheets

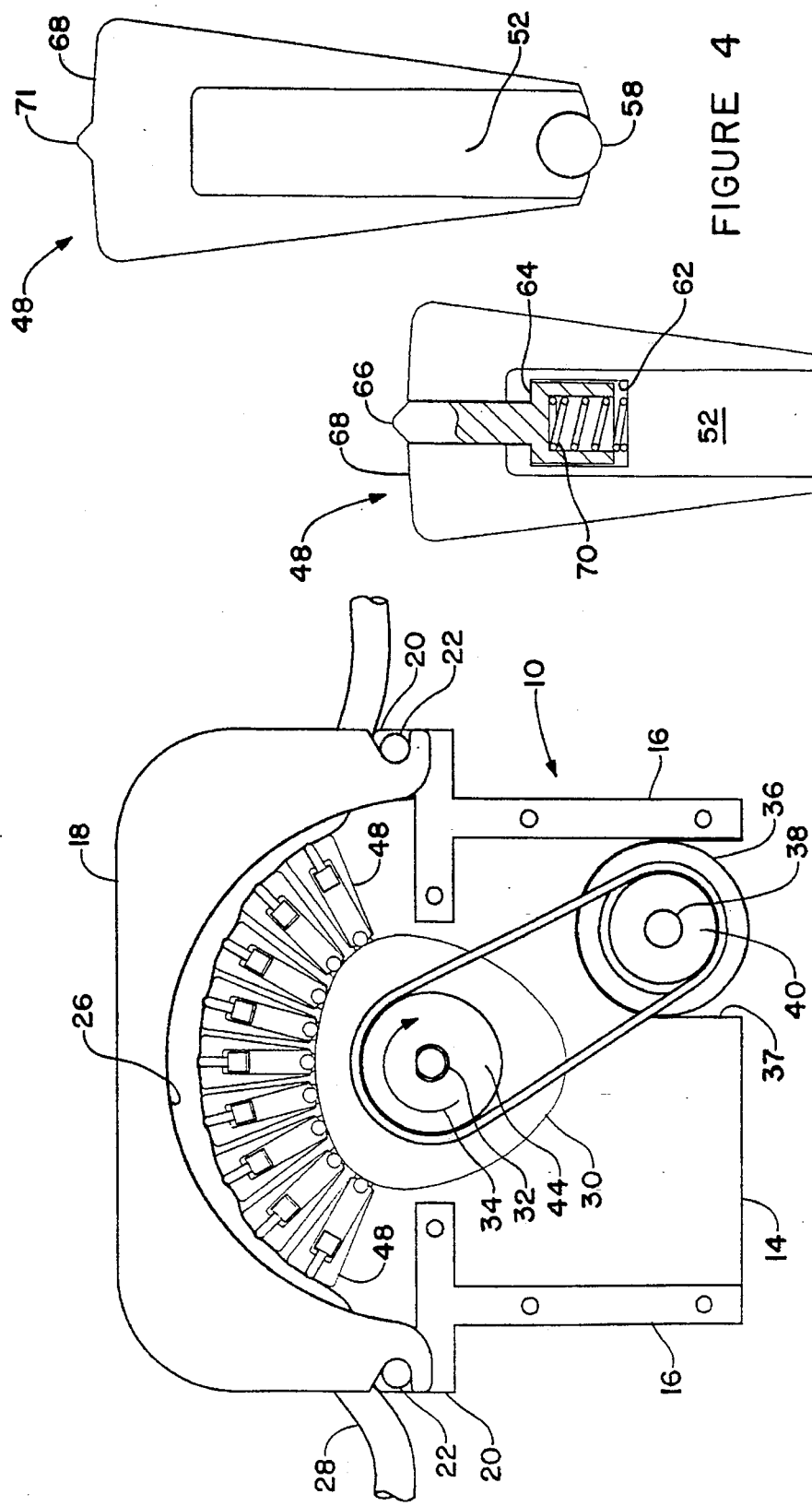

CURVILINEAR PERISTALTIC PUMP

BACKGROUND OF THE INVENTION

This invention relates in general to fluid pumps and more specifically to a peristaltic pump having a cam driven plurality of fingers for sequentially engaging a resilient tube to create liquid flow through the tube.

Conventional linear and rotary peristaltic pumps typically have a section of resilient tubing positioned between a wall and a set of rollers or reciprocating pushers that progressively compress sections of the tubing to pump liquids. Such pumps are often used in medical applications, such as intravenous infusion or withdrawing fluids such as in a wound drainage system. These pumps operate in a positive manner and are capable of generating substantial outlet pressures.

Typical linear peristaltic pumps include those described by Sorg et al. in U.S. Pat. No. 2,877,714, Borsannyi in U.S. Pat. No. 4,671,792 Heminway et al. in U.S. Pat. No. 4,893,991 and Canon in U.S. Pat. No. 4,728,265. While generally effective, these pumps are large, complex and cumbersome, requiring a drive shaft parallel to a resilient tube and a plurality of cams along the drive shaft to move pushers toward and away from the tube.

Rotary peristaltic pumps generally dispose a resilient tube along a circular path, with a number of rollers mounted around the circumference of a circular rotor sequentially rolling along the tube to occlude the tube and force liquid through the tube. Typical of such pumps are those disclosed by Soderquist et al. in U.S. Pat. No. 4,886,431 and Kling in U.S. Pat. No. 3,172,367. These pumps often have relatively low efficiency and impose high shear and tension stresses on the tube causing internal tube wall erosion or spallation. The tube may eventually be permanently deformed so that the tube becomes flattened into a more oval shape and carries less liquid.

Another type of peristaltic pump has a tube arranged along a circular path with a cam member within the circle sequentially moving a plurality of blunt pushers or fingers outwardly to sequentially compress the tube from one end of the path to the other. Typical of these pumps are those shown by Gonner in German Patent No. 2,152,352 and Tubospir in Italian Patent No. 582,797.

These pumps tend to be less complex than linear peristaltic pumps. However, the pressure imposed by the blunt fingers reduces tube life, sometimes causing internal tube wall erosion or spallation, which results in particulate matter getting into the fluid stream. Tube with different wall thicknesses cannot be accommodated by these pumps, since with thinner than standard tubes the fingers will not properly occlude the tube and with thicker than standard tubes the tube will close prematurely and be subject to excessive compression, requiring higher cam drive power and causing excessive wear on the cam and tube.

Thus, there is a continuing need for peristaltic pumps of greater simplicity, small size, low drive power requirements and which can accommodate resilient tubes of varying wall thickness while reducing wear and internal erosion of the resilient tube.

SUMMARY OF THE INVENTION

The above-noted problems, and others, are overcome in accordance with this invention by a curvilinear peristaltic pump having a concave curved, generally circular, platen for supporting a resilient tube, a multi-lobe cam rotatable about the center of the platen concavity, and a plurality of pump fingers riding on the cam as cam followers and guided to move in a radial direction toward and away from said platen.

Each pump finger has a face for engaging a tube on said circular platen. Each face includes a narrow pinch finger spring centered in the face and biased to extend beyond the face. Further, each pump finger includes a roller between the body of the pump finger and the cam to ride on the cam in the manner of a roller bearing, reducing wear.

When the cam is rotated, the pump finger closest to the highest area on the cam (widest lobe) in the direction of rotation will be moved outwardly in a radial direction to squeeze the tube against the platen. As the cam continues to rotate, the second pump finger will squeeze the tube as the pinch finger on the first pump finger occludes the tube, to force liquid in the tube to flow in the same direction as the cam rotates. As cam rotation continues, the subsequent fingers will sequentially squeeze the tube to push liquid and then occlude the tube. At the same time, the pump finger just behind the lobe will move away from the tube, allowing the tube to expand and fill with liquid. This sequence continues as cam rotation proceeds.

BRIEF DESCRIPTION OF THE DRAWING

Details of the invention, and of preferred embodiments thereof, will be further understood upon reference to the drawing, wherein:

FIG. 2 is a side elevation of the pump at the beginning of a pumping cycle with the casing closed and the near side casing removed to show the internal components;

FIG. 3 is a detail side elevation view of the pump finger assembly having a spring biased pinch finger and with the pinch finger partially cut-away; and FIG. 4 is a detail side elevation view of a pump finger with an alternate pinch finger embodiment.

DETAILED DESCRIPTION OF PREFERRED EMBODIMENTS

Figure 1:
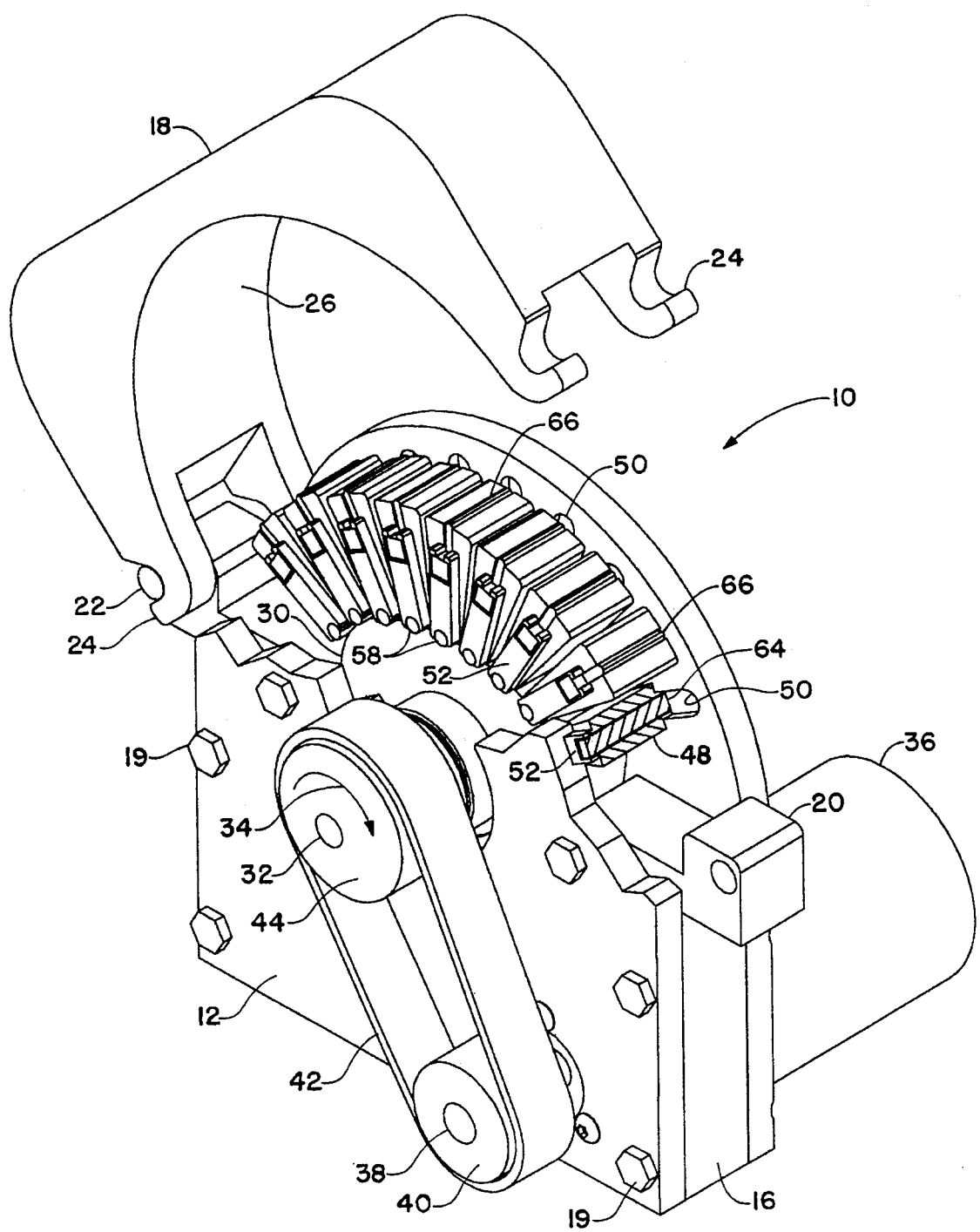
FIG. 1 is a perspective view of my pump with the casing open and partially cut-away and one pump finger and pinch finger cut-away.

Referring to FIGS. 1 and 2, there is seen a curvilinear peristaltic pump 10 having a casing basically consisting of a front plate 12, a back plate 14 and spacers 16. The casing is held together by a plurality of bolts 19 for ease of assembly and disassembly as needed. A removable cover 18 is secured to casing 10. Each spacer 16 includes a block 20 having a hole therethrough cooperating with a pin or bolt 22 and hook-shaped cover extensions 24 to hold the cover 18 in place.

Cover 18 includes a concave curvilinear platen 26. While platen 26 may have any suitable surface, generally a cylindrical surface is preferred. As best seen in FIGS. 2 and 3, a resilient tube 28 may be laid along platen 26, exiting through the open space between each pair of extensions 24.

A multi-lobed cam 30 is mounted for rotation about an axle 32 that extends through suitable bearings in front and back plates 12 and 14. Cam 30 may have any suitable number of lobes, two or more. For optimum performance with smallest size, the three-lobe cam shown is preferred. Where platen 26 is cylindrical, axle 32 is preferably at the axis of the platen. Cam 30 can be rotated in either direction to pump liquid through tube 28 in either direction. For convenience of operation explanation, cam 30 will be considered to be rotating clockwise, as indicated by arrow 34. Any suitable drive means may be used to rotate cam 30. In the preferred embodiment shown, an electric drive motor 36 extends through opening 37 in back plate 14 and is mounted on the back surface of front plate 12. Motor 36 has a drive shaft 38 extending through front plate 12 to a pulley 40. A drive belt 42 extends from pulley 40 to pulley 44 mounted on cam axle 32. Pulleys 40 and 44 are sized to provide the desired cam rotation speed. A variable speed motor 36 may be used to allow cam rotation speed to be easily varied. If desired, a gear system could be used in place of belt 42, or a different drive system could be used, such as a conventional hydraulic drive, in place of the electric motor and belt drive system shown.

A plurality of pump fingers 48, as best seen in FIGS. 1 and 3, are mounted for radial movement on front plate 12 and back plate 14 between cam 30 and platen 26. Any suitable number of pump fingers 48 may be used. Where a greater number of cam lobes are used, fewer fingers will generally be used. On the other hand, if narrow fingers 48 are used, a larger number may be provided. A large scale pump will generally use a larger number of fingers. A preferred number of pump fingers 48 for a three-lobe cam 30 of maximum efficiency coupled with small size is from 7 to 11 pump fingers, with 9 generally being optimum. As seen in FIG. 1, a plurality of opposed radial grooves 50 are provided in front plate 12 and back plate 14 to receive side extensions 52 that extend into grooves 50 and are freely movable therealong.

Each pump finger 48, as best seen in FIG. 3, includes a cylindrical recess 54 at a first end 56 for rotatably receiving a bearing roller 58. Rollers 58 freely roll on the surface of cam 30 in the manner of roller bearings, reducing wear on the cam surface. Side extensions 52 as seen in FIG. 1 are formed on the sides of pumping finger 48. A transverse, inverted "T" slot 62 is formed across the top of pump finger 48. A base 64 mounting a transverse pinch finger 66 fits within slot 62, with pinch finger 66 extending through a transverse cavity in the pumping surface along second end 68 of pump finger 48, as seen in FIG. 1. A spring 70 biases base 64 and pinch finger 66 toward the extended position.

The pump operates in the following manner. As seen in FIG. 2, two lobes of cam 30 are located at the beginning and end of the series of pump fingers 48. At this position, pump fingers 48 engaging the central portion of tube 28 along the middle of platen 26 are relatively withdrawn and those at the ends are relatively extended, thereby creating a zone of occlusion. Thus, the central portion of tube 28 is filled with liquid and the ends are substantially occluded. As cam 30 rotates in the direction of arrow 34, the second left pump finger 48 is pressed further against tube 28 while the rightmost pump finger begins to withdraw. Liquid is thus pushed in a zone of occlusion toward the right or outlet end of tube 28 and begins to exit. As cam rotation continues, pump fingers 48 are sequentially extended from the left and withdrawn at the right, forcing liquid in tube 28 toward the outlet end.

As seen in the central region of tube 28 in FIG. 2, pinch fingers 66 under the forces of springs 70 are relatively extended. The leftmost pump finger 48 is slightly extended, but second end 68 of pump finger 48 has not entirely occluded tube 28. Pinch finger 66 is extended sufficiently under the force of spring 70 to occlude the tube. With a thin wall tube 28, pinch fingers 66 will extend further to close the tube. With a thick walled tube, pinch finger will only extend a shorter distance until the tube is closed. Thus, only enough force is applied through the pinch finger to close the tube.

In prior art pumps, the pumping finger extended only a single preset distance under the strong mechanical force of a cam. With those arrangements, thin tubes are not entirely occluded and thick walled tubes are crushed beyond closure, often resulting in rapid wear, internal wall erosion and spallation with the resulting injection of particles of wall material into the liquid stream, of great concern in many infusion operations. Only a short degree of extension and retraction of pinch fingers 66 is required to produce this highly advantageous result, typically from about 0.2 to 1.0 mm.

FIG. 4 shows a side elevation view of a second embodiment of pump fingers 48. Here the pump fingers 48 use a pinch finger in the form of a fixed transverse ridge 71 across the surface 68 of the pump fingers in place of the spring biased pinch fingers 66 of the embodiment of FIG. 3. While the FIG. 3 embodiment is generally preferred for lowest tube wear and the ability to work well tubes of slightly varying diameter and wall thickness, in other cases the lower cost version of FIG. 4 may be preferred where the tube is more dimensionally uniform or the motor has sufficient power and the tube can take greater compression.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A curvilinear peristaltic pump which comprises:

a curved, concave, platen;

a rotatable cam spaced from said platen;

means for rotating said cam in a first direction;

a plurality of pump fingers, each having a first end riding on said cam and a second end adjacent to said platen;

guide means for axially guiding said pump fingers in radial directions;

said cam configured to first sequentially move said pump fingers toward said platen and second sequentially allow said pump fingers to move away from said platen;

each of said pump fingers having a pinch finger extending beyond said second end, transversely across second end;

whereby a resilient tube may be interposed between said platen and said second pump finger ends so that as said pump fingers are sequentially moved toward said platen, liquid in said tube will be pumped in said first cam rotation direction and each pinch finger will occlude said tube when each said pump finger reaches a position closest to said platen.

2. The curvilinear peristaltic pump according to claim 1 wherein each said pinch finger comprises a slidable member extending through a transverse slot in each pump finger second end and further including means for biasing each said pinch finger in a direction extending outwardly of said transverse slot.

3. The curvilinear peristaltic pump according to claim 2 wherein each of said pump fingers has a transverse cavity communicating with said transverse slot, a base member within said cavity supporting a pinch finger in said transverse slot, with a compression spring between said base member and a wall of said cavity opposite said pinch finger.

4. The curvilinear peristaltic pump according to claim 1 wherein each said pinch finger is a transverse ridge on each said pump finger second end.

5. The curvilinear peristaltic pump according to claim 1 wherein each of said cams has at least two lobes and has a surface gradually transitioning between lobes.

6. The curvilinear peristaltic pump according to claim 1 wherein each pump finger carries a rotatable roller at said first end to engage and roll along said cam.

7. The curvilinear peristaltic pump according to claim 1 further including releasable latch means for attaching said platen to a cam support casing.

8. The curvilinear peristaltic pump according to claim 1 wherein said platen surface is cylindrical and said cam is rotatable around an axis concentric with said cylindrical platen surface.

9. The curvilinear peristaltic pump according to claim 1 wherein said cam is supported for rotation between parallel front and back plates.

10. The curvilinear peristaltic pump according to claim 9 wherein said guide means comprises cooperating pairs of radial grooves in said front and back plates and side extensions on each pump finger for radial sliding in a pair of said grooves.

11. A curvilinear peristaltic pump which comprises:

a curved, concave, platen;

a rotatable multi-lobed cam spaced from said platen;

means for rotating said cam in a first direction;

a plurality of pump fingers, each having a first end riding on said cam and a second end adjacent to said platen;

guide means for axially guiding said pump fingers in radial directions from a center of rotation of said cam;

a resilient tube interposed between said platen and said pump fingers;

said cam configured to first sequentially move said pump fingers toward said platen to compress said tube and second sequentially allow said pump fingers to be moved away from said platen by tube resiliency;

each of said pump fingers sized to compress said tube as said cam moves said pump fingers forward said platen but not fully occlude said tube; and each of said pump fingers having a pinch finger extending transversely beyond said pump finger second end to fully occlude said tube as said cam moves said pump fingers toward said platen.

12. The curvilinear peristaltic pump according to claim 11 wherein each said pinch finger comprises a slidable member extending through a transverse slot in each pump finger second end and further including means for biasing each said pinch finger in a direction extending outwardly of said transverse slot.

13. The curvilinear peristaltic pump according to claim 11 wherein each said pinch finger is a transverse ridge on each said pump finger second end.

14. The curvilinear peristaltic pump according to claim 11 wherein said cam has at least two spaced lobes and cam diameter smoothly changes diameter from widest at said lobes to narrower between said lobes.

15. The curvilinear peristaltic pump according to claim 11 wherein each pump finger carries a rotatable roller at said first end to engage and roll along said cam.

16. The curvilinear peristaltic pump according to claim 11 further including releasable latch means for attaching said platen to a cam support casing.

17. The curvilinear peristaltic pump according to claim 11 wherein said platen surface is cylindrical and said cam is rotatable around an axis concentric with said cylindrical platen surface.

18. The curvilinear peristaltic pump according to claim 11 wherein said cam is supported for rotation between parallel front and back plates.

19. The curvilinear peristaltic pump according to claim 18 wherein said guide means comprises cooperating pairs of radial grooves in said front and back plates and further including side extensions on each pump finger for radial sliding in a pair of said grooves.

20. The curvilinear peristaltic pump according to claim 11 wherein each of said pump fingers comprises an elongated body having a transverse slot across said second end, extending into said pump finger and communicating with a cavity, said pinch finger slidably fitting within said slot and secured to a base in said cavity and further including a compression spring between said base and a wall of said cavity opposite said pinch finger to bias said pinch finger outwardly of said transverse slot.

* * * * *